United States Patent [19]

Sabee

[11] 4,360,398

[45] Nov. 23, 1982

[54] METHOD FOR APPLYING ELASTIC BANDS TO WEBS

[75] Inventor: Reinhardt N. Sabee, Appleton, Wis.

[73] Assignee: Sabee Products, Inc., Appleton, Wis.

[21] Appl. No.: 241,799

[22] Filed: Mar. 9, 1981

[51] Int. Cl.³ .............................................. B32B 31/08
[52] U.S. Cl. ................................. 156/164; 156/268; 156/270; 156/291; 156/324; 156/522; 156/548; 156/549; 156/554
[58] Field of Search ............... 156/164, 250, 253, 264, 156/265, 268, 269, 516, 520, 521, 522, 548, 549, 552, 567, 554, 270, 291, 324

[56] References Cited

U.S. PATENT DOCUMENTS

| | | | |
|---|---|---|---|
| 3,728,191 | 4/1973 | Wierzba et al. | 156/265 |
| 3,772,120 | 11/1973 | Radzins | 156/264 |
| 3,910,811 | 10/1975 | Paxton et al. | 156/521 |
| 4,081,301 | 3/1978 | Buell | 156/164 |
| 4,227,952 | 10/1980 | Sabee | 156/250 |
| 4,284,454 | 8/1981 | Joa | 156/265 |
| 4,285,747 | 8/1981 | Rega | 156/164 |
| 4,297,157 | 10/1981 | Van Vliet | 156/164 |

Primary Examiner—Jerome W. Massie
Attorney, Agent, or Firm—Henry C. Fuller

[57] ABSTRACT

The method and apparatus for applying elastic bands to a web for disposable products such as diapers includes the use of a rotating drum as a base or working surface to support the elastic bands and web while the bands are under tension and while adhesive is setting. Various arrangements are provided for gripping and holding the elastic bands to the drum surface, and various arrangements are provided for cutting the elastic ribbons in the waistband portions of the diapers to remove portions of the ribbon.

19 Claims, 19 Drawing Figures

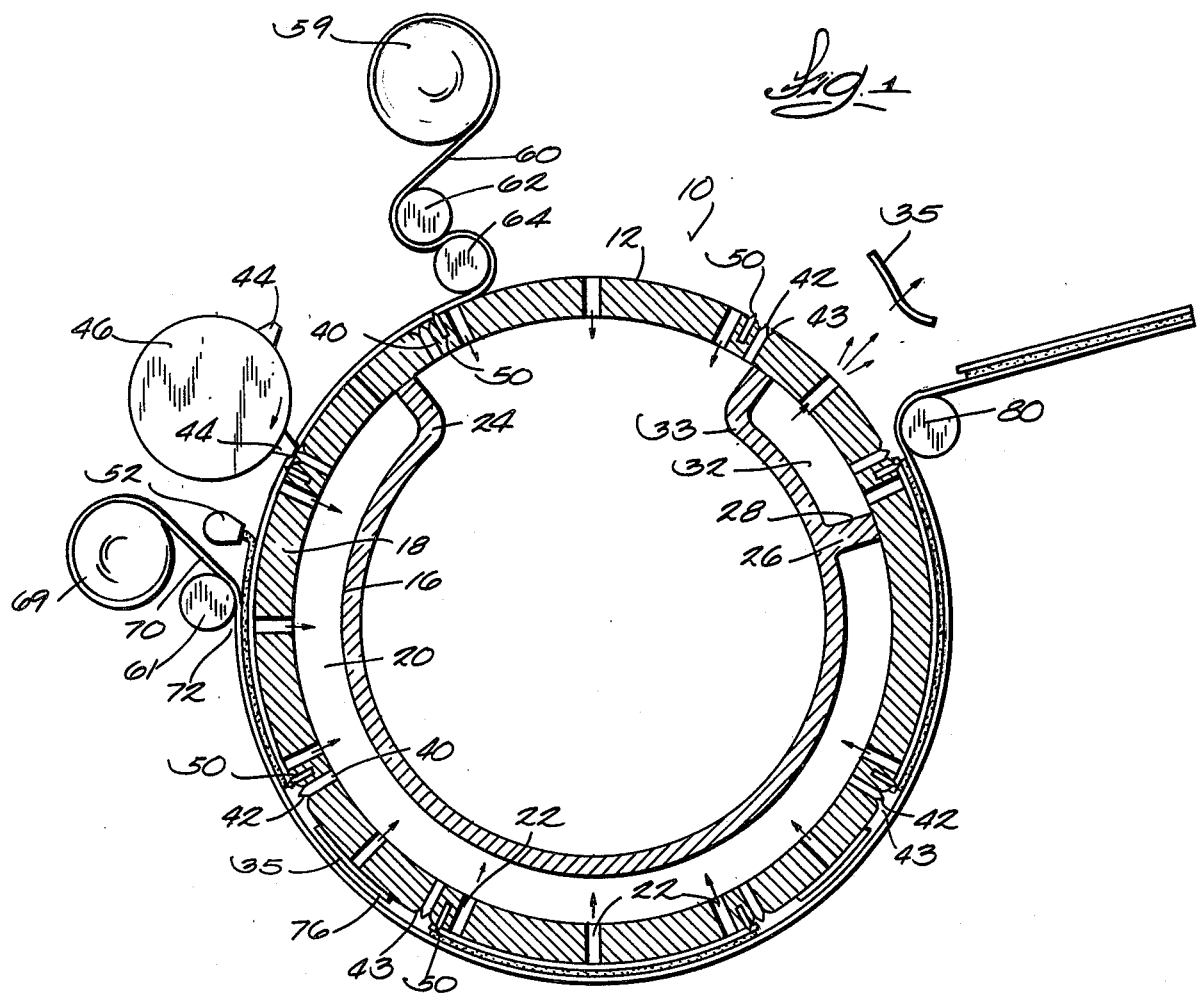
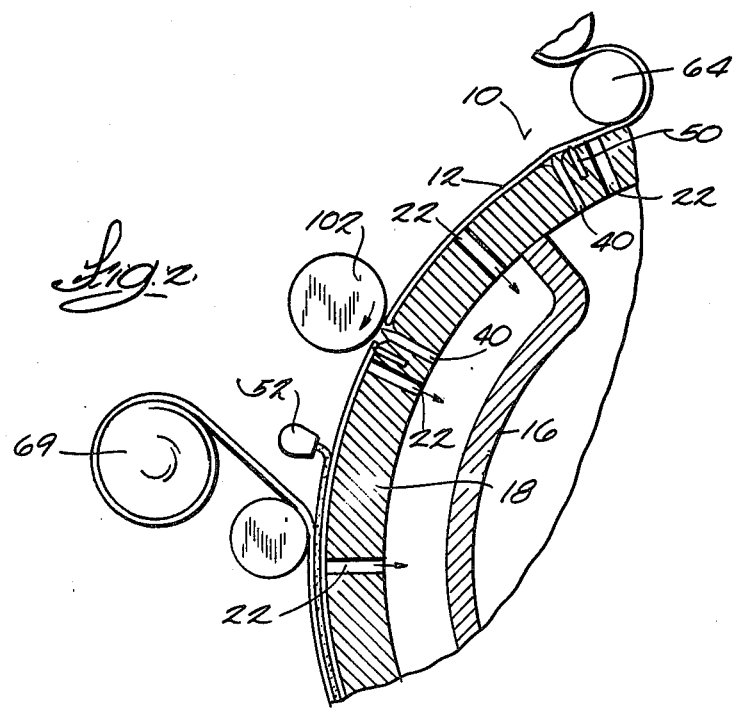

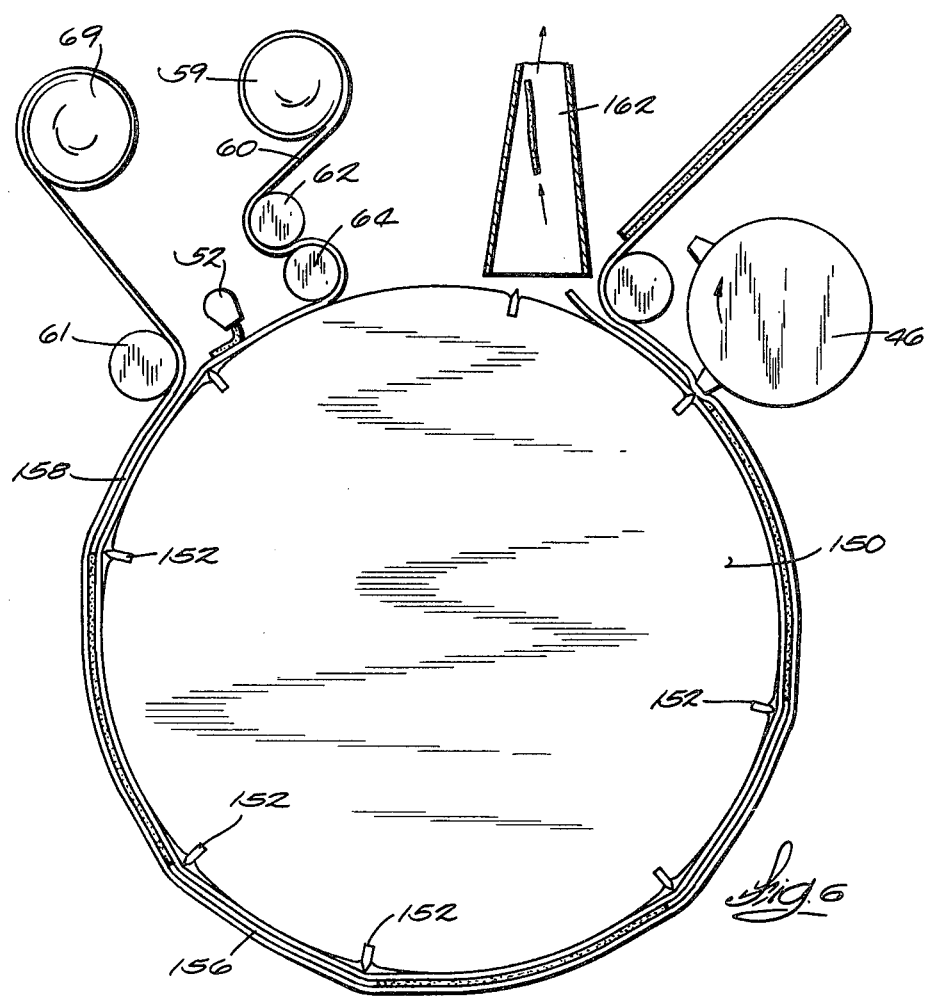
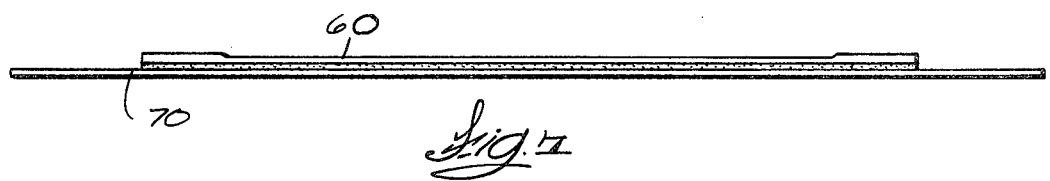

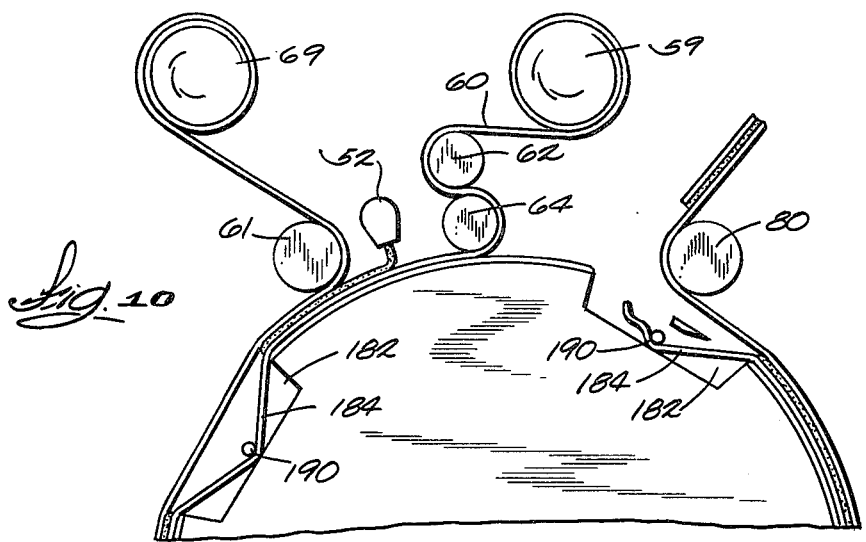
fig. 10
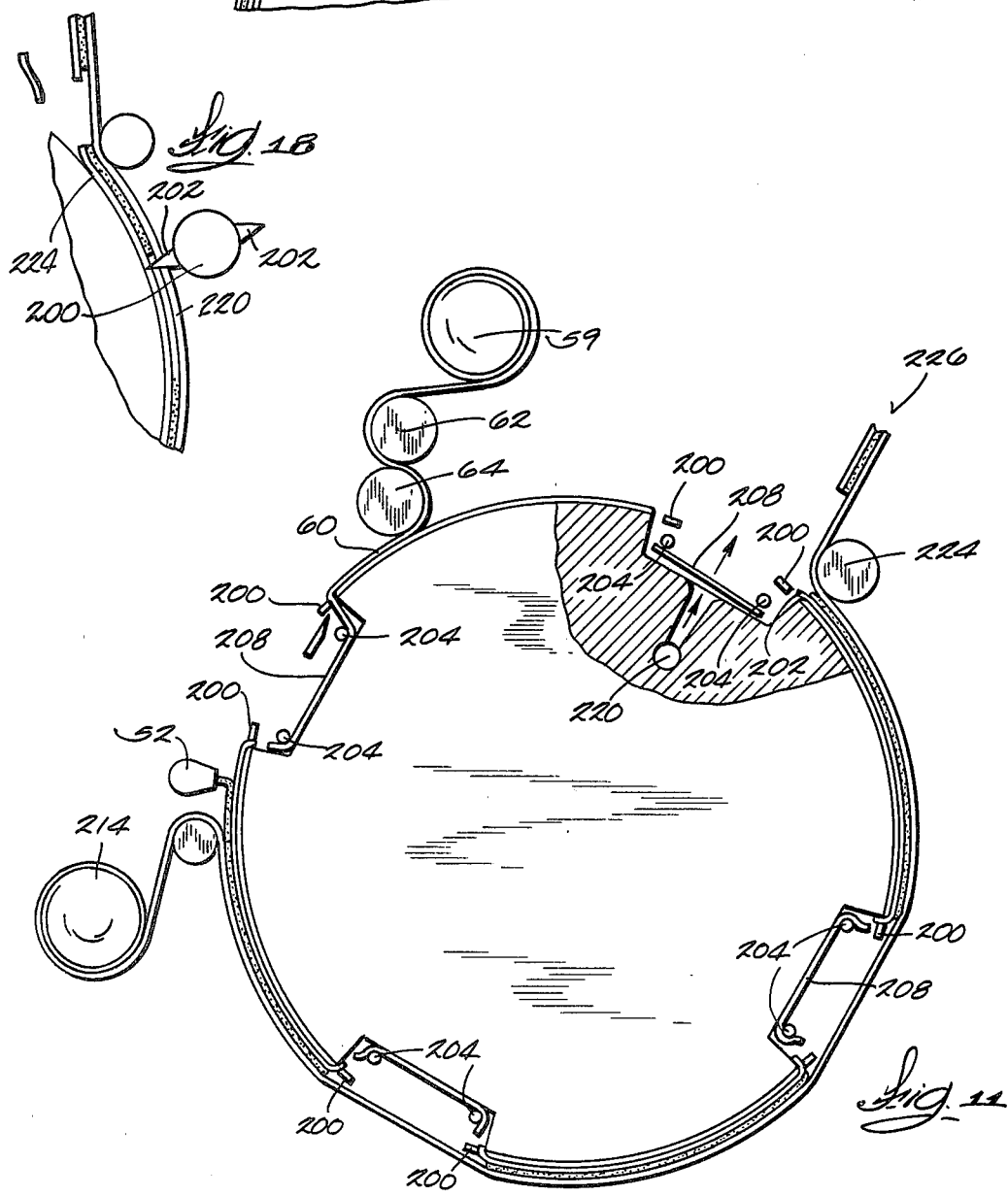
fig. 1B
fig. 11

METHOD FOR APPLYING ELASTIC BANDS TO WEBS

BACKGROUND OF THE INVENTION

Various techniques have been developed for applying elastic ribbons to webs to provide an elasticized leg portion in a disposable diaper. U.S. Pat. Nos. 4,081,301; 4,239,578 and my U.S. Pat. No. 4,227,952 and the patents cited therein are illustrative of the known methods.

SUMMARY OF THE INVENTION

The invention relates to method and apparatus for making disposable diapers with elasticized leg contacting portions in the diaper and more specifically to method and apparatus for applying the elastic bands to the backing or facing sheet. The difficulties in prior art methods, including handling discrete lengths of elastic ribbon with adhesive applied are overcome by a method which employs a base surface for supporting the elastic bands while the adhesive is applied and while the bands are under tension. The elastic ribbons are held on the assembly station base surface, which in the preferred embodiment is the periphery of a rotating drum by various techniques including vacuum and mechanical gripping devices or its own tension or the tension of facing and backing webs. The elastic bands are cut into the desired length either before or after the backing or facing web to which the elastic bands are adhered is fed to the drum supporting surface. Alternately, the supporting surface can be a series of interconnected plates.

The cut off of the elastic bands to the desired length is accomplished by knives and cooperating anvil rolls or anvil bars, with either the anvil bar or knife located on the drum and the other cooperating part located on a rotating wheel located close to the drum supporting surface.

After the web with adhered elastic ribbons leaves the drum, the absorbent pads and second web, which can be the other of a facing or backing sheet, is applied and the composite assembly is cut off to form individual diapers.

In some embodiments the belt tension of an auxiliary belt having a run wrapped around the periphery of the drum is employed to maintain tension or pressure on the elastic bands and the web backing or facing until the adhesive sets.

Further objects, advantages and features of the invention will become apparent from the disclosure.

DESCRIPTION OF THE DRAWINGS

FIG. 1 is a diagrammatic sectional view of apparatus for performing the method of the invention.

FIG. 2 is a fragmentary diagrammatic view of a modified embodiment.

FIG. 1A is an edge view of the web with applied band.

FIG. 2 is a fragmentary diagrammatic view of a modified embodiment of the apparatus shown in FIG. 1.

FIG. 6 is a diagrammatic perspective view of an alternate embodiment.

FIG. 7 is an edge view of the plastic band and backing or facing sheet laminate with the ends relaxed.

FIG. 10 is a diagrammatic view of a further embodiment.

FIG. 11 is a diagrammatic sectional view of an additional embodiment.

FIG. 18 is a fragmentary view similar to FIG. 12 with the web overlaying the ribbon.

DESCRIPTION OF THE PREFERRED EMBODIMENT

Figure 5:
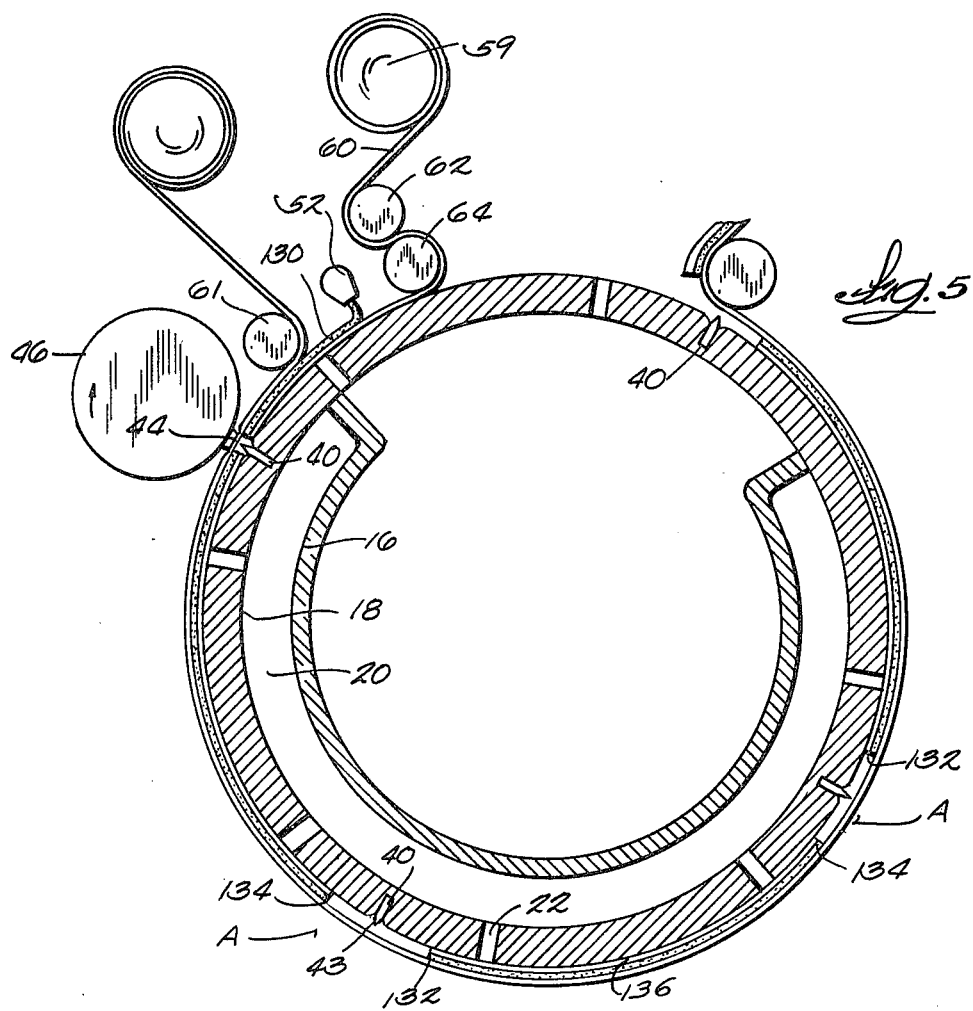
FIG. 5 is a diagrammatic sectional view of a further modified embodiment.

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

FIG. 1 shows apparatus used for practicing the invention which includes a drum 10 having a peripheral surface 12 which serves as the base surface support or working surface for accomplishing the application of adhesive to elastic band, cutting the elastic band to length and assembling the elastic bands, the backing and facing sheet. The drum includes wall portions 16 and 18 which define a toroidal vacuum chamber 20 which communicates with the periphery 12 through vacuum passages 22. The vacuum passages 22 communicate with the portion of arc of travel of the drum between end walls 24 and 26. The unadhered severed elastic ends can be discharged (as subsequently described in more detail) from the drum by pressure chamber 32 formed between walls 28 and 33. As illustrated in FIG. 1, an unadhered end 35 is discharged from the drum surface after the web with adhered elastic bands leaves the periphery of the drum over roller 80, as hereinafter described.

The drum structure illustrated in FIG. 1 also includes a plurality of fixed knives 40 which are circumferentially arranged about the drum and project in a radial direction with respect to the axis of the drum. The knives have a cutting edge 42 located in a cavity or recess 43 in the periphery 12 of the drum. The knives 40 cooperate with anvil bars 44 carried by rotating anvil bar holder 46 which rotates in timed sequence to position an anvil bar 44 in the recess to coact with the knives 40 as the recesses move past the anvil holder 46. Inasmuch as two elastic bands are employed, the assembly shown in FIG. 1 only represents the equipment used to handle one elastic band. Duplicate equipment would be at a point spaced axially of the drum from that shown in FIG. 1.

The drum in FIG. 1 also includes gripper pins 50 which are spaced in position to assist in positively locating the applied piece of ribbons on the drum during the operational sequence of work performed on the drum. An adhesive applicator 52 applies beads of adhesive to the elastic ribbons. The term "gripping means" as used in the claims includes the use of vacuum, pins, fingers, belts and the tension of the backing or facing webs.

In use, pairs of elastic bands or ribbons 60 are drawn from parent rollers 59 and applied in an axially spaced arrangement on the drum by guide rollers 62 and 64. Rollers 64 apply the elastic ribbon 60 under tension. The ribbons 60 are positioned on the anchoring pins 50 and held in place on the drum by the suction at the vacuum ducts 22. As the drum 12 rotates, the elastic bands are severed by the knives 40 and anvil bars 44 and the cut ribbons are carried past the adhesive applicators 52 and beads of adhesive are applied.

Subsequently, the plastic backing or the facing sheet or web 70 is drawn from parent roll 69 and applied to the elastic bands at point 72. The adhesive is applied only to a length of elastic ribbon which is desired for the crotch portion and not applied to the equivalent lengths for the waistband portions. Accordingly, portions of the elastic band, such as portion 35, relax because they are no longer held under tension and no adhesive has been applied. These portions 35 are subsequently ejected after the web with adhered ribbons is removed from the drum over roller 80.

FIG. 2 shows a somewhat different cutting arrangement in which the knives 40 project past the periphery of the base surface 12 and cooperate with a smooth anvil roller 102 to accomplish the cutting function.

Figure 3:
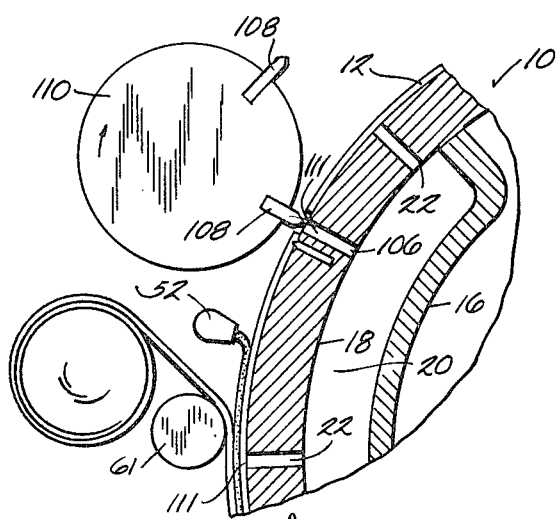
FIG. 3 is a fragmentary perspective view of a further modified embodiment.

FIG. 3 shows equipment similar to FIGS. 1 and 2, but the anvil bars 106 are carried by the drum and the cut off knives 108 are carried by a knife roll 110. Anvil bars 106 can have a surface 111 which has the same radius as the periphery of the drum.

Figure 4:
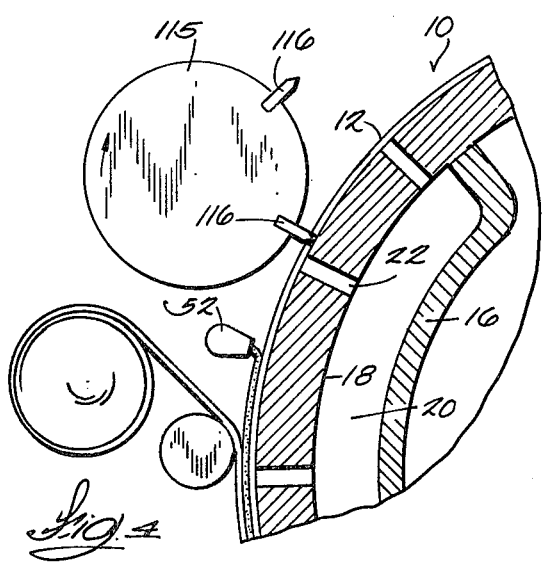
FIG. 4 is a fragmentary diagrammatic sectional view of a further modified embodiment.

FIG. 4 shows a cut off assembly used with the apparatus shown in FIG. 1 in which a knife roll 115 carries a plurality of knives 116 which cuts the elastic bands against the base surface 12 of the drum 10.

FIG. 5 shows a portion of the drum and associated equipment where there is no projecting pins. Vacuum gripping combined with tension of backing or facing webs are employed to maintain the ribbon or elastic band on the periphery of the drum. In FIG. 5, the drum has knives 40 similar to those in FIG. 1 located in recesses 43 in the periphery of the drum. The knives 40 project beyond the periphery of the drum and cooperate with a rotating anvil roll 46 and anvil bars 44. In the structure disclosed in FIG. 5, the knives 40 sever the elastic ribbon while under tension. In FIG. 5, the anvil roll and knives perform the cut on the spaced elastic ribbons after the web has been applied. The feed roll 61 pinches the applied backing or facing web against the elastic band segment 130 to maintain tension between the roll 61 and the feed roll 64. When the cut has been made, the ends 132 and 134 of the elastic bands relax and become thicker, as shown in FIG. 7, because the adhesive is not yet set and, as shown at point A on the drum periphery, the relaxed ends 132 and 134 have separated and, although they are adhesively adhered, there is no tension. The vacuum ducts or suction passages 22, however, secure the elastic ribbon to the drum periphery to maintain tension on the ribbon segment 136 in between the relaxed ends. The gap between the ends 132 and 134 becomes the waistband portion of the diaper.

FIG. 6 shows a drum 150 with a plurality of spaced knives 152 and a web feed roll 64 and elastic band feed roll 69. The anvil roller 46 causes cut off of the elastic ribbon after the adhesive has set and just prior to removal of the web and applied adhesive band assembly from the drum. The adhesive is applied to portions of the elastic ribbon by applicators 52 so that there are gaps 156 and 158 between the applied glue segments, with the gaps 156 and 158 providing waistband portions which do not have elastic bands similar to FIG. 1A. Tension of the elastic ribbon on the drum holds the elastic bands in place until the glue has set and the cut off is made. The non-adhered portions of the elastic band can be removed by suction removal device 162. The adhesive can be applied intermittently for the length of the adhered portion of the elastic band.

FIG. 7 shows a section of the web and ribbon assembly produced by the method of and apparatus shown in FIG. 5.

Figure 8:
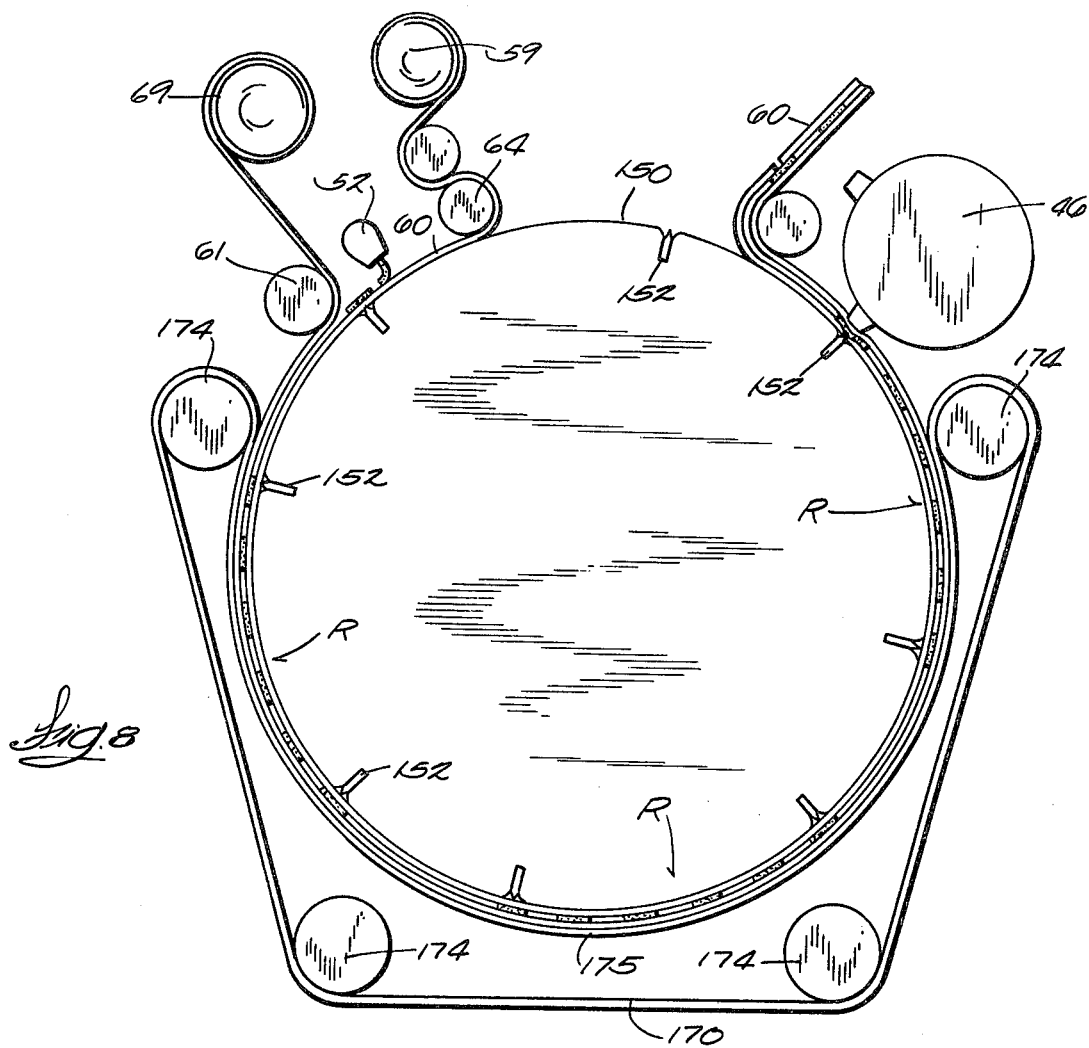
FIG. 8 is a diagrammatic sectional view of a further embodiment.

In FIG. 8 the drum 150 employs an endless belt 170 trained around rollers 174, which has a working run 175 pressed against the drum 150, to provide tension to maintain the stretched condition with the elastic ribbon 60 until the adhesive supplied by applicator 52 sets. The adhesive can be applied continuously at spaced locations at zone R. The absence of glue will result in separated independent relaxed segments at each end of the adhered portions when the plastic ribbon is cut by cooperation of the anvil roller 46 and cutting knives 152.

Figure 9:
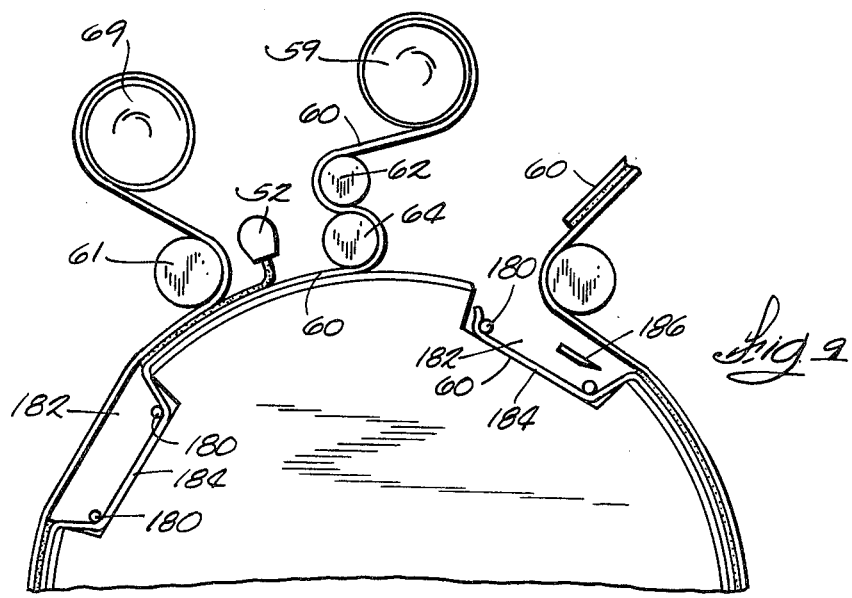
FIG. 9 is a fragmentary diagrammatic view of a further embodiment.

In the embodiment illustrated in FIG. 9, the elastic band 60 is held against the drum by grippers 180 located in recesses 182. Thus, glue supplied by the glue applicator 52 is not applied to the portions 184 of the elastic band located within the recesses. The elastic ribbon 60, which does not have glue applied, can be cut by a stationary knife 186 which clears the inside of the drum surface.

FIG. 10 is similar to FIG. 9 except that a single gripper 190 is employed in the recess 182. There are no projections above the base surface and the elastic band is depressed in the groove to provide unadhered ends which can be removed by vacuum.

In the arrangement shown in FIG. 11, double gripper clamping bars 200 anchor the ends 202 of the elastic band to the drum and double gripper bars 204 hold the elastic band segments 208 which are severed from the web of elastic ribbon to form the waistband portions. The glue is then applied by an applicator to the elastic band portions on the surface of the drum and then a backing or facing sheet is applied from the parent roll 214. An air pressure nozzle at 220 can be employed to eject the severed segments 208 from the recesses after the gripper bars 204 are released. The clamping bars 200 are released adjacent the take-away roller 224 which conveys the assembly 226 away from the drum.

Figure 12:
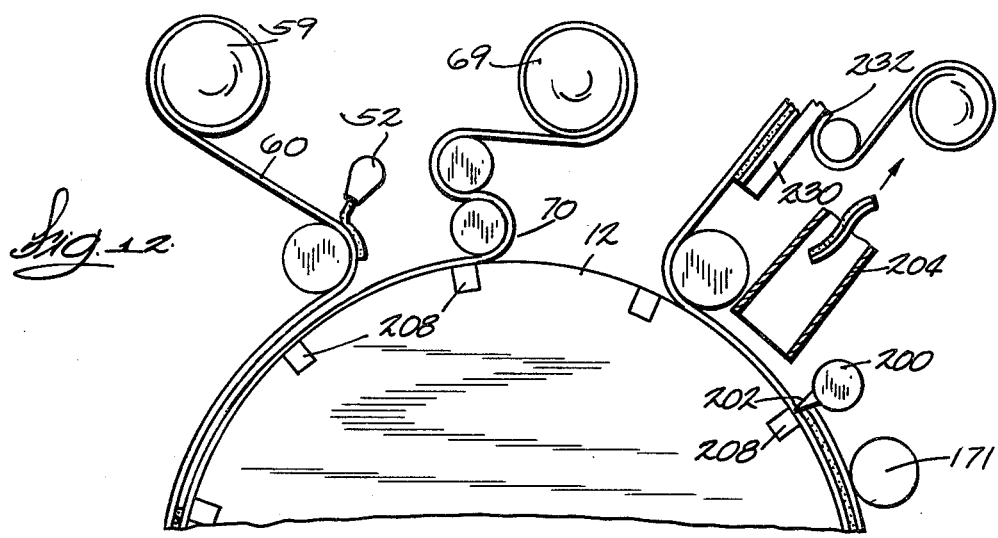
FIG. 12 is a diagrammatic view of a further embodiment of apparatus to practice the invention.
Figure 13:
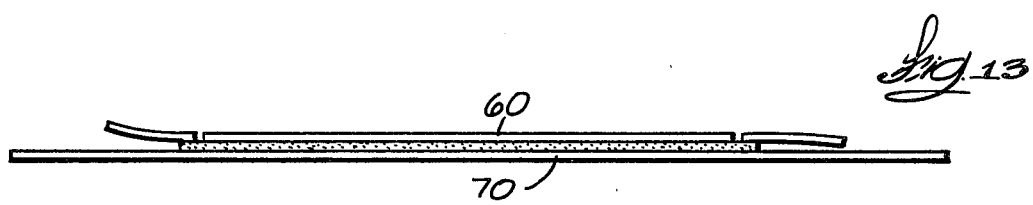
FIG. 13 is a diagrammatic edge view of elastic band applied to the web by apparatus shown in FIG. 8.
Figure 14:
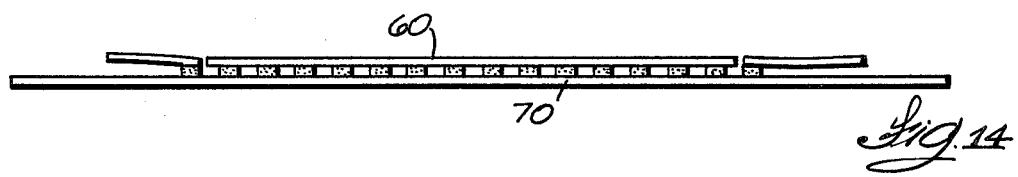
FIG. 14 is a view similar to FIG. 13 with the glue applied intermittently in a pattern.
Figure 15:
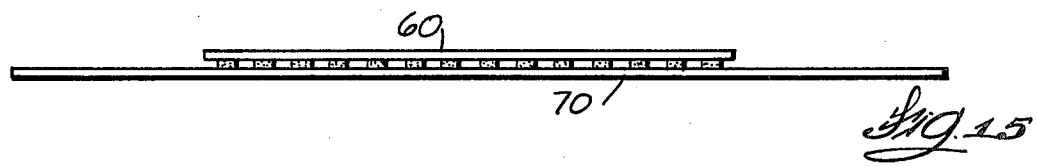
FIG. 15 is a diagrammatic view similar to FIG. 1A with the glue applied intermittently in a pattern.
Figure 16:
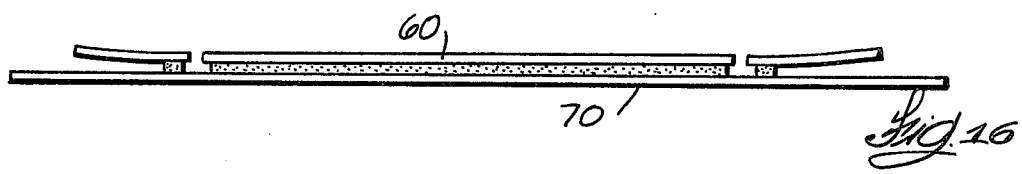
FIG. 16 is a view similar to FIG. 13 with the glue applied differently.
Figure 17:
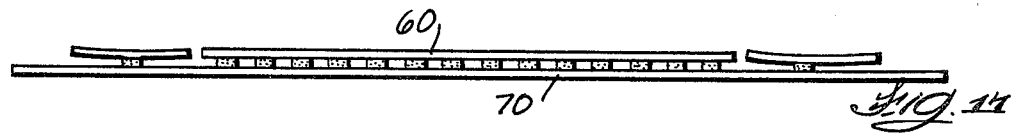
FIG. 17 is a view similar to FIG. 13 with the glue applied in a further pattern.

FIG. 12 is a further embodiment of apparatus for practicing the invention. In this embodiment the film 70, either backing or facing material, lies between the elastic ribbon 60 and the drum surface 12. Glue is provided by an applicator 52 to the elastic ribbon prior to deposit of the ribbon on the film. A squeeze roll 171, similar to that illustrated in FIG. 8 can be employed to maintain tension and hold the elastic band against the film until the adhesive sets. The glue is provided intermittently and, in the areas where there is no glue, the elastic band is severed from the adhered portions by the rotary cut-off knife 200 which has one or more cutting blades 202 which pinches against the elastic ribbon which is under tension and may or may not provide a small nick or slit in the plastic film. The plastic backing does not provide any waterproofing function at this location in a diaper and a mark or even a small slit is immaterial with respect to the functioning of the finished product. Cutting the ribbon against the plastic film simplifies the apparatus considerably and allows much higher speeds than could be obtained otherwise. The severed elastic ribbon sections can be taken away from the working area by a vacuum assist. The drum periphery 12 can be provided with spaced anvil bars 208, as illustrated. Alternatively, the knife can pinch against the periphery of the drum.

FIG. 18 shows a further modification of the FIG. 12 arrangement in which the film 220 overlies the elastic ribbon 224 and the knife pierces the backing or facing material 220 with a small slit prior to cutting the non-adhered portion 224 of the elastic ribbon from the ribbon web assembly. Again, the slit in the backing or facing sheet would not be in a zone which is subject to leakage. Of the various embodiments illustrated herein, it is believed at this time that the apparatus illustrated in FIGS. 6, 12 and 18 are the preferred embodiments for high speed operation.

The FIGS. 13 through 17 illustrate various combinations of dots, dashes and spaces which may be obtained in a glue pattern by adjusting the timing of the adhesive applicator. As is apparent, products may be produced with no unadhered ends, with unadhered ends of equal or unequal lengths or relaxed adhered ends of the elastic ribbon to the underlying web.

As illustrated in FIG. 12, after the elastic ribbon and web is withdrawn from the drum, the absorbent pads 230 can be applied and the other of the facing and backing sheets 232 can be superimposed.

Inasmuch as the cutting blades 202 of the knife 200 in FIGS. 12 and 18 is relatively narrow and only slightly wider than the elastic, the slits in the facing or backing are quite small and do not present any problem with respect to leakage as noted above.

I claim:

1. A method for intermittently attaching lengths of elastic ribbon to spaced portions of a moving web comprising the steps of:
   (a) feeding a stretched elastic ribbon to an elastic ribbon applying station having a base surface;
   (b) holding said stretched elastic ribbon on the base surface;
   (c) applying adhesive to discrete portions of said stretched elastic ribbon;
   (d) feeding a web of substantially inelastic material to said ribbon applying station;
   (e) adhering the lengths of stretched elastic ribbon to isolated portions of said inelastic web; and
   (f) maintaining at least a portion of said elastic ribbon in a stretched condition until the adhesive sets and cutting a non-adhered portion of said elastic ribbon by pressing cutting means simultaneously against the ribbon and a portion of the width of the web so as to sever only the ribbon.

2. The method of claim 1 in which the step of feeding a web of substantially inelastic material to said station precedes the step of feeding an elastic ribbon to the station.

3. The method of claim 1 wherein said base surface comprises a periphery of a drum.

4. The method of claim 3 wherein said holding step includes a vacuum chamber for holding the elastic bands on the working surface.

5. The method of claim 1 wherein said cutting step forms one of a slit and a mark on said web where the ribbon is cut.

6. A method for contiuously attaching discrete lengths of elastic ribbon to isolated portions of a moving, substantially inelastic web of interconnected articles to impart an elasticized character to predetermined, isolated portions of said articles while preserving the substantially inelastic character of said articles in areas where said ribbon is unattached to said web, said method comprising the steps of:
   (a) feeding an elastic ribbon to an assembly station in a stretched condition;
   (b) providing a base surface at the assembly station;
   (c) holding said stretched elastic ribbon in predetermined locations on a base surface;
   (d) applying adhesive to discrete lengths of said stretched elastic ribbon at predetermined intervals along the length of said ribbon while said stretched elastic ribbon is supported by the assembly station base surface;
   (e) feeding a web of interconnected articles comprised of a substantially inelastic material to said assembly station;
   (f) adhering the discrete lengths of stretched elastic ribbon to predetermined, isolated portions of the articles comprising said web at said assembly station in the discrete areas of said elastic ribbon having adhesive applied thereto; and
   (g) maintaining portions of said elastic ribbon in a stretched condition at least until said adhesive sets up;
   (h) cutting said elastic ribbon transversely by applying cutting means agains both the ribbon and the web in the same cutting plane to make a cut of a width sufficient to sever the ribbon but not the web.

7. A method for continuously attaching discrete lengths of elastic ribbon to isolated portions of a moving, substantially inelastic web of interconnected articles to impart an elasticized character to predetermined, isolated portions of said articles while preserving the substantially inelastic character of said articles in areas where said ribbon is unattached to said web, said method comprising the steps of:
   (a) feeding an elastic ribbon to an assembly station in a stretched condition;
   (b) applying adhesive to discrete lengths of said stretched elastic ribbon at predetermined intervals along the length of said ribbon;
   (c) feeding a web of interconnected articles to said assembly station;
   (d) adhering the discrete lengths of stretched elastic ribbon to predetermined, isolated portions of the articles on said web at said assembly station in the discrete areas of said elastic ribbon having adhesive applied thereto;
   (e) maintaining at least portions of said elastic ribbon in a stretched condition at least until said adhesive sets up; and
   (f) cutting said elastic ribbon adjacent at least one end of the discrete lengths of adhered elastic ribbon, thereby severing the unadhered portions of said elastic ribbon by simultaneously applying cutting means against both the ribbon and the web in the same cutting plane to make a cut of a width sufficient to sever the ribbon but not the web.

8. A method for making disposable diapers, said method comprising the steps of:
   (a) feeding an elastic ribbon to a rotating surface at an assembly station under tension;
   (b) holding said ribbon on said rotating surface;
   (c) applying adhesive to said stretched elastic ribbon at predetermined intervals along the length of said ribbon;
   (d) feeding a web to said assembly station;
   (e) adhering the stretched elastic ribbon to predetermined, isolated portions of the web;
   (f) maintaining at least portions of said elastic ribbon in a stretched condition at least until said adhesive sets up;
   (g) cutting said elastic ribbon adjacent at least one end of the discrete lengths of adhered elastic ribbon, thereby severing the unadhered portions of said elastic ribbon by pressing cutting means against both the ribbon and the web in the same cutting plane at a point which does not afford leakage to make a narrow cut which will sever the ribbon but not the web;
   (h) applying an absorbent pad to said ribbon-web lamina;
   (i) applying the other of a backing and facing sheet; and
   (j) cutting individual diapers from the assembled web by a cut which cuts the entire width of the web.

9. A method for attaching lenghts of elastic ribbon to spaced portions of a moving web comprising the steps of:
   (a) feeding an elastic ribbon to an elastic ribbon applying station having a base surface;
   (b) applying adhesive to discrete portion of said ribbon;
   (c) maintaining said elastic ribbon under tension on the base surface for the steps (d), (e) and (f);
   (d) feeding a web of substantially inelastic material to said ribbon applying station;
   (e) adhering the lengths of stretched elastic ribbon to isolated portions of said inelastic web;
   (f) maintaining at least a portion of said elastic ribbon in a stretched condition until the adhesive sets; and
   (g) cutting a non-adhered portion of said elastic ribbon by simultaneously pressing cutting means against the elastic ribbon and web at the point where the ribbon is cut to cut said ribbon.

10. The method of claim 9 wherein said elastic ribbon is superimposed on said web and said web is against said base surface.

11. The method of claim 9 wherein said elastic ribbon is against said base surface and said web is between said cutting means and said elastic ribbon and said cutting means leaves cuts in said web as it cuts said ribbon.

12. The method of claim 10 wherein said web is cut by said cutting means adjacent the cut in the ribbon when the ribbon is cut.

13. The method of claim 9 in which said base surface is the surface of a cylindrical drum and web tension maintains said web against said drum surface.

14. The method of claim 9 in which said base surface has an anvil and said web is against said anveil and said ribbon overlies said web when said ribbon is cut.

15. The method of claim 9 in which said base surface has an anvil and said ribbon is against said anvil and said web overlies said ribbon when said ribbon is cut.

16. The method of claim 9 in which said base surface constitutes the peripheral surface of a drum and cutting means on said drum and on the anvil roll arranged to cooperate with said cutting means to perform the cutting step of said ribbon when said web and ribbon are between said cutting knife and said anvil roll.

17. The method of any of claims 1, 6, 7, 8 or 9 wherein said cutting step is performed by pressing one of a knife and anvil against the ribbon and web, with the other of the knife and anvil being supported on the base surface and under the web and ribbon.

18. The method of any of claims 1, 6, 7, 8 or 9 wherein said cutting step is performed by pressing a knife against the web and ribbon, with the knife forming a slit in the web and severing the ribbon.

19. The method of any of claims 1, 6, 7, 8 or 9 wherein said cutting step is performed by a knife which severs the ribbon and marks the web as the knife is pressed against the ribbon and web.

* * * * *